(12) United States Patent
Williams et al.

(10) Patent No.: US 7,182,726 B2
(45) Date of Patent: *Feb. 27, 2007

(54) BRACHYTHERAPY DEVICE AND METHOD

(76) Inventors: John I. Williams, 2307 Forest Park Blvd., Fort Wayne, IN (US) 46825; Marc G. Apple, 1606 Sycamore Hills Dr., Fort Wayne, IN (US) 46804

( * ) Notice: Subject to any disclaimer, the term of this patent is extended or adjusted under 35 U.S.C. 154(b) by 95 days.

This patent is subject to a terminal disclaimer.

(21) Appl. No.: 10/421,141

(22) Filed: Apr. 24, 2003

(65) Prior Publication Data

US 2003/0233136 A1    Dec. 18, 2003

(51) Int. Cl.
*A61N 5/00*    (2006.01)

(52) U.S. Cl. .......................................... 600/3

(58) Field of Classification Search ............... 600/1–8, 600/437; 623/11.11, 18.11, 22.11, 23.11, 623/66.11, 12.11; 424/1.25, 1.11, 2.31, 449; 606/108, 194; 128/899; 604/19; 427/2.1
See application file for complete search history.

(56) References Cited

U.S. PATENT DOCUMENTS

| | | | | |
|---|---|---|---|---|
| 4,222,374 A | * | 9/1980 | Sampson et al. | 128/899 |
| 4,946,435 A | * | 8/1990 | Suthanthiran et al. | 600/3 |
| 5,342,283 A | * | 8/1994 | Good | 600/8 |
| 5,795,286 A | * | 8/1998 | Fischell et al. | 600/3 |
| 5,871,708 A | * | 2/1999 | Park et al. | 424/1.25 |
| 6,120,540 A | * | 9/2000 | Apple et al. | 623/11.11 |
| 6,183,409 B1 | * | 2/2001 | Armini | 600/3 |
| 6,224,610 B1 | * | 5/2001 | Ferrera | 606/108 |
| 6,287,249 B1 | * | 9/2001 | Tam et al. | 600/3 |
| 6,293,899 B1 | * | 9/2001 | Sioshansi et al. | 600/3 |
| 6,350,226 B1 | * | 2/2002 | Fischell et al. | 600/1 |
| 6,749,553 B2 | * | 6/2004 | Brauckman et al. | 600/3 |
| 2003/0225331 A1 | * | 12/2003 | Diederich et al. | 600/437 |
| 2004/0265475 A1 | * | 12/2004 | Hossainy et al. | 427/2.1 |

* cited by examiner

*Primary Examiner*—John P. Lacyk
(74) *Attorney, Agent, or Firm*—Taylor & Aust, P.C.

(57) ABSTRACT

The present invention provides a system and method of applying low dose, localized radiotherapy which is effective to reduce or eliminate the formation of post-operative scar tissue at surgical sites, such as an epidural site after spinal surgery. In an exemplary embodiment, a device is implantable before closing a surgical site as a barrier, the device being designed to deliver a desired therapeutic amount of energy to particular tissue. The device can be a barrier layer, seed containment unit, radiospike, or catheter. The energy may be provided by the material of the device itself, or may be provided by an external source, such as by circulating radioactive fluid through the device itself. Various embodiments include additional components of the device which deliver drug or chemical agents to targeted tissue and/or shield components to prevent dosage to non-targeted tissue.

2 Claims, 5 Drawing Sheets

BRACHYTHERAPY DEVICE AND METHOD

This Application claims priority under PCT/US02/18804, entitled "Brachytherapy Device and Method," filed on Jun. 14, 2002, and U.S. Provisional Application 60/297,962, entitled "Brachytherapy Device and Method," filed on Jun. 13, 2001.

FIELD OF THE INVENTION

The present invention generally relates to energy therapy with brachytherapy systems, and the invention more particularly relates to devices and methods for localized treatment to minimize postoperative fibrosis/scarring at a variety of bodily sites, such as an epidural site. It also relates to devices and methods to treat cartilaginous (articular or discal) pathology in order to reduce pain or improve function.

BACKGROUND OF THE INVENTION

Surgical intervention is an established and effective treatment modality to manage acute and chronic spine abnormalities for which direct intervention can mechanically alter and alleviate anatomic dysmorphic elements, secondary injury responses, and functional inhibitions from autoimmune or inflammatory diseases.

More specifically, surgical treatment in the form of decompressions (e.g. discectomy, laminotomy, laminectomy) and/or fusion, is often performed on one or more levels of the human spine to ameliorate or alleviate symptoms originating from disc herniation, foraminal and/or central stenosis, instability secondary to post-traumatic, degenerative, congenital, iatrogenic, or idiopathic conditions, epidural fibrosis, adhesive arachnoiditis, and compressive radiculopathy and myelopathy resulting from any form of space occupying lesion. Outcomes may not always be optimal to eliminate pain and/or spinal dysfunction. In fact, delayed recurrent pain and functional decline can often follow initial uncomplicated surgery in an average of 20–25% of patients, and up to as many as 40% of patients in some historical clinical series.

The healing response after primary laminectomy, and especially following revision procedures, often results in variable amounts of epidural and perineural scar or fibrosis formation at the surgical site. Excessive fibrotic tissue may proliferate about the exposed dura mater or adhere to the adjacent nerve roots and structures. Symptoms and complications from such scar tissue have been implicated as the cause of 25–50% of the patients that are collectively categorized as those experiencing "failed back surgery syndrome" (FBSS). Furthermore, clinical studies demonstrate a direct causative relationship may exist between postoperative epidural scarring and recurring radicular pain to the involved nerves at the surgical site.

Various drug treatments have been tested in animals, and in a more limited degree in people, in an effort to inhibit or minimize post-laminectomy scar formation. These have included parenteral and/or intravenous administration of non-steroidal anti-inflammatory drugs or corticosteroid agents, as well as local administration via pre-invocation of these agents upon an extrinsic membrane or polymer direct placement into the surgical bed. Often materials have included soft or solid biologic or nonbiologic "layering" agents and materials to act as barriers to suppress fibrosis. However, these methods and materials have thus far demonstrated limited clinical human success and/or may actually create secondary side effects themselves such as poor wound healing, infection/abscess, and promotion of hemorrhage.

Low dose ionizing radiotherapy has long been clinically established to minimize or prevent post surgical scarring from keloid, hyper inflammatory responses in arthritic diseases, and to inhibit postoperative heterotopic ossification after hip or elbow arthroplasty. More recently, such techniques have been applied to reduce post angioplasty induced arterial restenosis from hyperplastic scar response.

Marc Apple, a co-inventor of the present invention, is also a co-inventor of several patents and a pending PCT application involving the application of therapeutic energy, preferably radiation energy, to a target internally to a patient, to minimize exposure of healthy tissue to the therapeutic energy dosage. Various mechanisms for delivering the therapeutic energy are used, including a catheter, a prosthetic implant, or a member attached to the prosthetic implant. PCT Application PCT/US01/45,689 (Apple et al.) entitled "Directional Energy Emitting Implant" discloses a device that is attached to a prosthetic device. The device is effective in reducing heterotopic ossification caused by the implant, inhibiting growth or migration of benign or malignant living cells, and minimizing infectious processes and scar formation induced from surgical placement of the prosthesis or fixation device. U.S. Pat. No. 6,120,540 (Apple et al.) entitled "Radio Prosthesis" discloses an implant device for delivering a dosage of radiation to targeted tissue, such as a prosthetic hip. A therapeutic energy source material is positioned either on or within a prosthetic device. The implant system is particularly useful for inhibiting heterotopic ossification. U.S. Pat. No. 6,162,165 (Apple et al.) entitled "Medical Radiation Treatment Device;" U.S. Pat. No. 6,159,141 (Apple et al.) entitled "Medical Radiation Treatment Delivery Apparatus;" U.S. Pat. No. 6,117,064 (Apple et al.) entitled "Catheter System;" and U.S. Pat. No. 5,916,143 (Apple et al.) entitled "Brachytherapy Catheter System" disclose various catheters for administering radiation internal to a patient. A radiation carrier material such as an inert radioactive gas for the treatment of restenosis after angioplasty, and malignancies is inside the catheter.

However, a need exists for an improved low dose ionizing radiotherapy system for patients requiring spinal surgery.

SUMMARY OF THE INVENTION

The present invention provides a system and method of applying low dose, localized, ionizing radiotherapy and/or other forms of combined therapeutic energy therapy, in order to reduce or eliminate the formation of post-operative scarring, particularly epidural scar formation.

One preferred embodiment of the brachytherapy device of the present invention is effective in reducing epidural scar tissue resulting from spinal surgery, thereby creating a dural adhesion barrier. More particularly, the present invention provides an implantable device which can be safely and strategically placed at the time of spinal surgery, or percutaneously via guided trans-spinal placement, in order to administer a controlled dose of radiation energy. The energy is delivered to a specific region of soft tissue adjacent the spinal cord to minimize postoperative epidural (and possibly intraneural) fibrosis and/or excessive fibroblastic activity about the dura mater and neural elements of the spine. The invention may also be implemented in surgical sites at other areas of the body. Additionally disclosed herein is a new perispinal/paraspinal radiotherapy treatment method and insertable catheter-type devices useful for executing such treatments to prevent dural adhesions or create a dural adhesion barrier.

Disclosed are various devices constructed in accordance with the present invention for emitting and delivering the proper energy dosage at the desired site for the intended effect. Other preferred embodiments of the brachytherapy device of the present invention device may be provided in the form of a layer, seed, radiospike, or any structure that is shaped, adapted and formed of a material having appropriate physical properties to reside at the vicinity of the laminectomy procedure without causing undesired interference with surrounding tissue. For example, a layer embodiment can be provided in a predetermined shape and/or in a sheet which can be custom cut as needed before or during a surgery for implantation at the surgical site.

For an enhanced effect, variations of the invention provide concomitant therapy with drug delivery, application of a magnetic field and/or ultrasonic energy. For example, the invention provides a system that includes an implantable, moderate to high frequency transducer placed at the time of surgery to deliver a desired energy field to a targeted spinal, paraspinal, or other postoperative site. This system may include one or more adjacent implantable barrier layers which focus, direct or repel the energy as desired. Additionally, another optional therapy according to the invention provides a fluid radionuclide delivery system including an implantable catheter adapted to reside in the spinal environment. Optionally, embodiments are provided which co-integrate a separate unit, layer, or module to optimize the homogenous energy delivery, and optional integrated drug delivery to targeted areas while minimizing dosages to adjacent, non-targeted normal tissues.

The devices and treatment of the present invention are engineered specifically to target an appropriate dose of radiation energy to diminish the quantity and/or density of postoperative fibrosis in the vicinity of the spine, spinal cord, or other post-operative sites, including carpal tunnel sites.

An advantage of the present invention is that it provides a treatment that eliminates or reduces a recurrence of spinal cord or nerve compression and the related undesirable symptoms due to scarring at the site of spinal surgery. As a result, patients and physicians alike benefit from reduced symptoms, complications, and a reduced likelihood of a need for revision surgery. A further benefit is that the energy reduces the possibility of infection and/or hypersensitivity with hyper inflammation.

While the systems set forth herein are described in conjunction with the delivery of radiation therapy for purposes of illustration, it is expressly understood that the principles set forth herein are all applicable to a broad range of other therapeutic energy sources, including but not limited to ionizing radiation, high-frequency ultrasound, hyperthermic emissions, electromagnetic fields, and their combination.

Also, many of the embodiments of the invention are directed to such treatment in the spinal area for purposes of illustration. However, it is expressly understood that the devices, methods and systems described herein may be used for treating other areas of the body, and that such devices, methods and systems are within the scope of the invention. Additionally, disclosed herein is a catheter system particularly designed for a transpinal/paraspinal treatment of chronic back pain or other ailments.

For a more complete understanding of the brachytherapy device and method of the present invention, reference is made to the following detailed description and accompanying drawings in which the presently preferred embodiments of the invention are shown by way of example. As the invention may be embodied in many forms without departing from spirit of essential characteristics thereof, it is expressly understood that the drawings are for purposes of illustration and description only, and are not intended as a definition of the limits of the invention. Throughout the description, like reference numbers refer to the same component throughout the several views.

DETAILED DESCRIPTION OF THE DRAWINGS

Now referring to the Figures, wherein like numerals designate like components, FIGS. 1–11 illustrate various devices constructed in accordance with teachings of the invention for administering treatment to patients. The invention is broadly directed to devices and methods for reducing post-operative scarring and fibrosis at bodily tissue sites.

A. Radio-Coordinated Dural Anti-Adhesion Barrier

Figure 1:
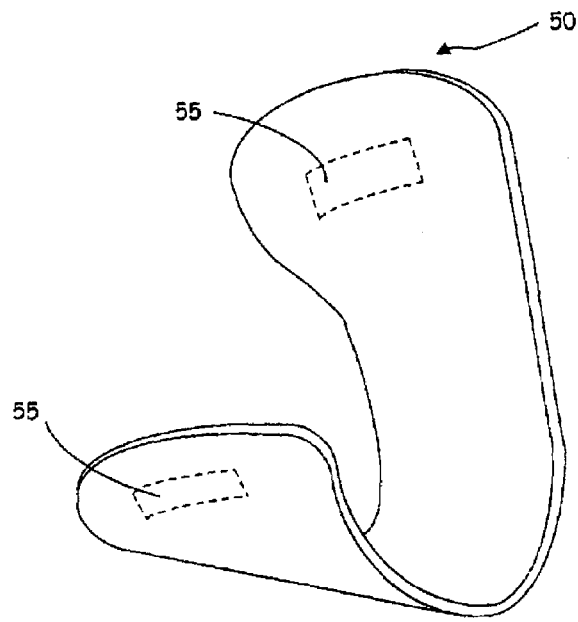
FIG. 1 is a perspective view of a precut implantable device constructed in accordance with teachings of the invention, the device having orientation information indicated thereon.
Figure 4:
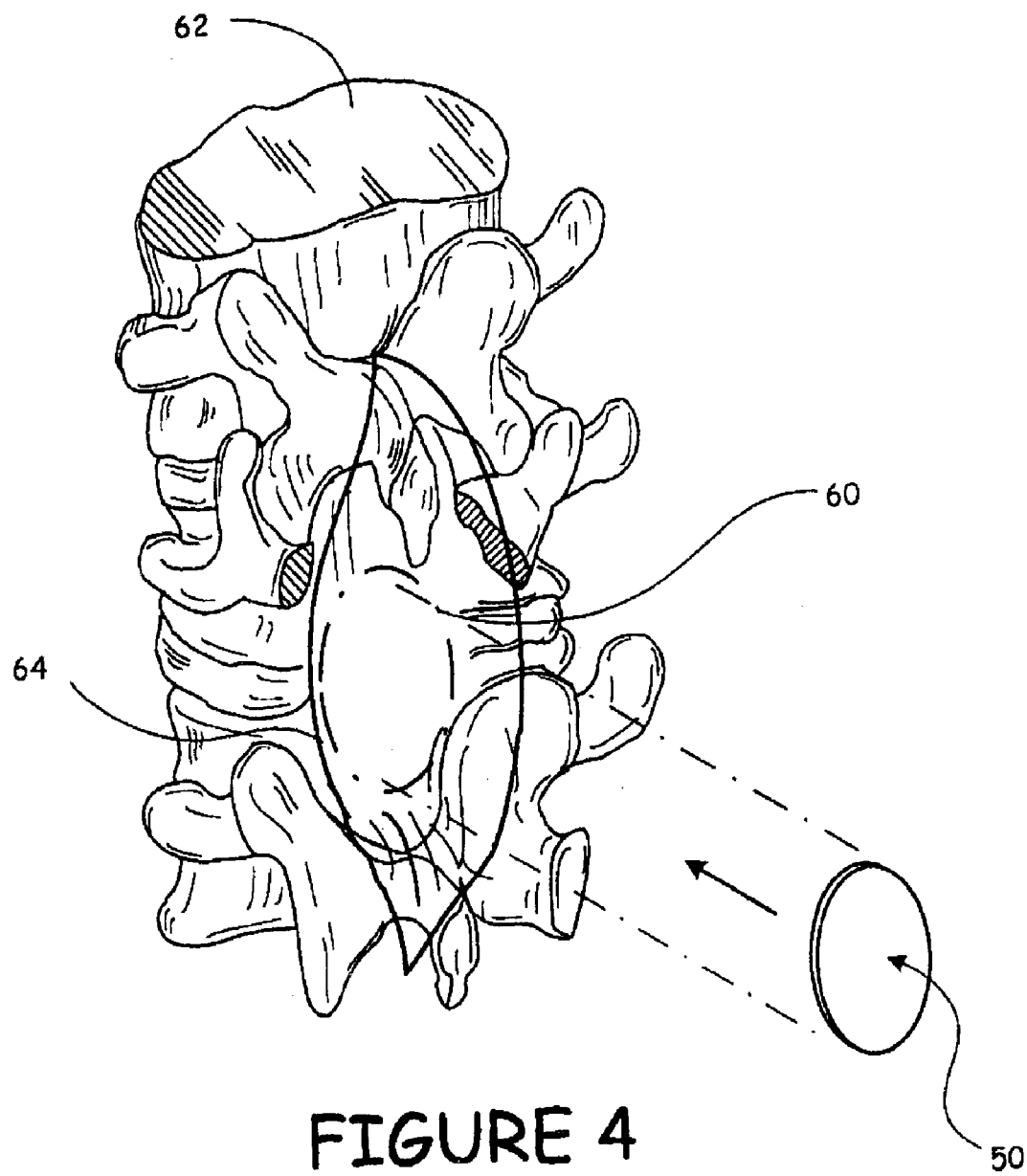
FIG. 4 is a perspective view of a laminectomy surgical site and an implantable device according to an embodiment of the invention, dashed lines indicating the placement of the device at the site.

Providing an implantable device for treatment of a targeted tissue area, FIG. 1 illustrates an implantable radiotherapy layer or dural anti-adhesion barrier device 50 according an exemplary embodiment of the invention. The device 50 is especially adapted for surgical placement to a specific post-operative site, such as epidural site after a laminectomy procedure prior to closing, as illustrated in FIG. 4, wherein the device 50 is placed adjacent the dura 60 and/or spine 62 prior to a closing of the incision 64. In particular, the device 50 is configured to emit radiation energy at a rate, duration and area to optimally reduce or eliminate post laminectomy fibrosis in the epidural vicinity of the surgical site.

Figure 3:
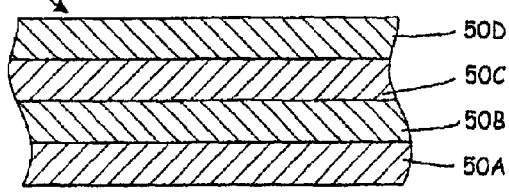
FIG. 3 is a fragmentary, sectional view of an implantable device having multiple layers.

In the exemplary embodiment illustrated in FIG. 1, the implantable radiotherapy device 50 includes a single or composite layer which may be capable of pre-implantation shaping. The device 50 may be constructed of multiple composite layers 50A, 50B, 50C, and 50D as illustrated in FIG. 3, described below in greater detail, wherein various respective layers, portions of layers, or other elements provide desired physical characteristics and/or treatment effects to surrounding tissue. The device 50 may be provided in a variety of shapes, materials and properties, as will be explained herein. It will be apparent to those skilled in the art that the configuration of the particular device of the invention may be varied depending on the particular application and circumstances in order to effect a desired treatment.

Figure 2:
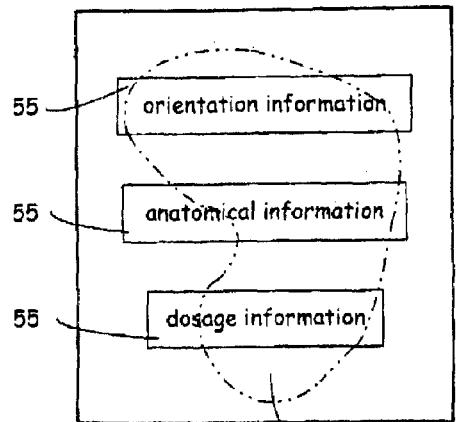
FIG. 2 is a plan view of a blank layer, dashed lines indicating an area from which a desired implantable device could be cut and having orientation information indicated thereon.

The layer-shaped device 50 is a palpable, pre-formed single or multi-layer biocompatible unit. The device 50 may be provided in a pre-fixed shape (square, rectangle, oval, etc.), or alternatively, as illustrated in FIG. 2, as a sheet 50' intended to be custom cut to a needed dimension prior to or during surgery prior to being implanted. In order to adapt to various needs, the layered device 50 may be flexible or be constructed to have varying degrees of compliant stiffness. In an application wherein the device must be anchored, fixation elements (not shown) may be provided to secure the device 50 in a fixed implanted location.

The implantable device 50 may be integrated into a "targeted" position within or adjacent to resected spinal bone, extremity bone, or related soft tissue as to provide a beneficial three dimensional orientation in order to administer a therapeutic dose of energy (radiation), with or without concomitant or sequential anti-inflammatory medication or a controlled magnetic field.

In effect, this therapeutic radioemitting device 50, also provides a functional and measurable dural adhesion barrier, when applied for spinal related procedures, thereby enhancing dural adhesion control, fundamentally from the ionizing or other emitted radiation, due to the reduction in stimulatory cytokines and related fibroblastic cascade response to surgical injury/trauma and inflammatory response which creates excessive fibrosis (scarring). Secondarily, previously described co-administered drugs/agents and/or magnetic field induction are meant to be adjunctive or synergistic in support to the tissue/cellular hyperproliferative inhibition by radiation either by affecting different but collaborative inflammatory cellular mediators and/or assisting to concentrate (by field attraction or repelling) or protective normal tissue deflection of radioemissions.

1. Externally Visible Indicators

The various implantable devices described herein, including the layer shaped device 50 of FIGS. 1 and 2 and the further devices to be described below, preferably include externally visible indicators. For example, referring to FIGS. 1 and 2, the layer shaped device 50 preferably includes external labels 55 to assist the surgeon to select a device 50 appropriately configured for a particular application and/or to direct accurate in vivo placement as with respect to important orientation information, e.g., superior, inferior, lateral, medial, anterior, dorsal, and rotational orientation relative to the surrounding tissue. While the labels may include printed words, numbers or phrases, the device 50 could include other types of externally visible indicators as well, such as bumps, dots, nicks, colors, symbols, etc.

Additionally, the shape of the device itself can indicate to a trained surgeon the proper placement of the device 50 with respect to routinely identifiable anatomic landmarks encountered in the surgical environment. Accordingly, it is intended that such external markings and shape indicators aid to facilitate reproducible and predictable directional control of emitted radiation and expected dose rate, total dose, and depth dose profile.

Ideally, this could provide a "conformal" radiation dose by optimizing dose homogeneity to the intended target tissue (i.e. the soft tissue space and exposed nerve regions desired to inhibit reactive fibrosis) while minimizing the dose and volume of exposure to normal adjacent tissue, potentially much more efficiently than external beam radiotherapy techniques.

Additionally, radio-opaque markers composed of metal, metal alloys, radioactive nuclides or related parent or daughter isotopes, etc. are preferably positioned and fashioned as similar for function and intent as the visible or palpable markers, except that they provide a visible confirmation of the position and orientation of the components by x-ray via fluoroscopy or hard copy x-ray or equivalent. This can provide measurement assessment and 2 dimensional or 3-dimensional positional identification of the components as well as confirmatory calculations of expected radiation dose to the adjacent tissue.

2. Primary Materials and Radionuclides

A radiotherapy device 50 according to the invention may be constructed of a wide variety of primary base materials compatible for implantation with surrounding tissue. The primary base materials preferably include, for example, plastics, natural or synthetic rubbers, metals, metal-alloys, bio-compatible molecular chain compounds, allogenic or heterogenic natural or synthetic dissoluble compounds when in vivo (natural human, animal, or plant byproduct materials), viton rubber, polyurethane, polyethylene, polyimide, polyvinylchloride, polyamide, polytetrafluoroethylene, and silicone.

Specific external or internal channels (upon the barrier) may be conducive to placement of a radionuclide source, before, during, or after in vivo placement of the delivery unit. The radiation energy emitted by the source may be localized ionizing, fluorescent, luminescent, high frequency ultrasonic, or thermal radiation energy. This may include concomitant administration within a controlled, local magnetic field which has been integrated into the device apparatus either to synergistically inhibit fibrosis and/or hyper-inflammation with the beneficial effects of radiation and/or with the effects of anti-inflammatory drugs (cortico or non-corticosteriods), cell mitosis inhibitors with chemotherapeutic agents such as Taxol or the like.

The energy source of the implantable device 50 includes a radionuclide component. In the multiple-layer device 50 illustrated in FIG. 3, one or more of the layers, e.g., layer 50B, contains the radionuclide component. Suitable radionuclides include any humanly compatible and therapeutically effective solid, liquid, gas, gel, or other intermediate phase radio nuclide or radioisotope compounds which emit gamma rays, x-rays, beta particles, alpha particles, positrons, auger electrons, photons, or any combination thereof produced by nuclear decay, isomeric transition, electron capture, fluorescent, phosphorescent or luminescent induction, external bombardment activation, electrical stimulation or any combination thereof. In one preferred embodiment, the radionuclide containing device or dissolves in vivo after the radiotherapy dose is administered. Specific primary radionuclides, either in stable or radioactive form, include but are not limited to xenon, krypton, neon, argon, radon, technetium, rhenium, yttrium, phosphorus, iodine, strontium, samarium, gold, copper, palladium, iridium, tin, rubidium, osmium, platinum, ytterbium, cesium, americium, radium, thallium, chromium, vanadium, barium, titanium, bismuth, and rhodium. More particularly, the specific primary radionuclides of choice are yttrium, strontium, iridium, iodine, palladium, cesium, xenon, rhenium and phosphorus.

The utilization and integration of any of these isotopes are applied to the device to enhance individual energy emissions and tissue penetration, in vivo safety, half-life decay properties and specific activities or concentrations of materials. A near ideal effect on the target tissue and depth is thereby achieved with regard to dose rate, depth dose, total does, and elimination rates. The preferred dose rates deliver energy in the range of 50 to 250 cGy/hr. Acceptable dose rates also include from 10 to below 50 cGy/hr and above 250 to 500 cGy/hr. Dose rates in the order of magnitude of from 10 to 200 cGy/min may be of benefit, if the half-life and millicuries of radioactivity can be short (several minutes) and low respectively or radio-material has a short dwell time and is removed. Dose rates per millicurie are between 0.5 cGy/min and 200 cGy/min mCi.

The total dose delivered to the targeted tissue is preferably between 700 cGy and 2000 cGy. Also, an acceptable total dose is from 200 to below 700 cGy, and above 2000 to 3500 cGy. The total dose to nontargeted soft tissue and bone tissue is preferably up to 500 cGy, but dosages of up to 1500 are acceptable. The radio-dose prescription is precalibrated for each specific application site and marked directly on the implantable device. This would be intended to deliver a fixed dose and dose rate range.

3. Attenuating Barrier Components

To facilitate a precise directional focusing of energy to targeted tissue, and to shield desired areas of adjacent non-targeted tissue from unnecessary exposure, an optional embodiment of the device includes one or more radio attenuating barrier element. Such barriers can include one or more indwelling or externally contoured radio attenuating elements and/or layers. For example, as mentioned above, FIG. 3 shows a sectional view of an embodiment of the device 50 which includes multiple composite layers, and one of these layers, e.g., 50A, may be a radio attenuating layer or segment thereof localizing radio opaque elements in specific orientation may be present internally or externally, to demarcate pre and post operative orientation for confirmation of radiation dose delivery and simulation planning.

Such a barrier element may be activated at the time immediately after placement or in delay at recovery or bedside, post-anesthesia. As used herein, "activation" refers to an intended active step taken to expose previously placed radionuclide containing components, or delayed placement into the modules of a radionuclide source, or placement via an attached or separated intermediary catheter-type component such that a partial or complete electrical or light generated radiation emitting device may be after loaded for a finite period of time.

Visible external markings are preferably provided on the device to demarcate the barrier areas and/or the radioemitting areas to guide the surgeon to implant the device at a proper orientation and alignment.

4. Drug or Chemical Agent Component

To provide supplemental postoperative treatment of the site, a radioemitting device is provided according to an optional embodiment which includes an integrated drug or chemical agent selected for a desired treatment effect. Referring, for example, to FIGS. 1 and 2, the device 50 may have a surface impregnated with an agent, or the device 50 may include one or more layers 50C, D including such agents, as illustrated in FIG. 3. The device preferably includes time released dissolvable layers in specific alignment to the radioemitting component. For example, desirable medical agents may include Taxol, 5-FU, platinum based drugs, vincristine, NSAIDS, or corticosteriods, solely or in combination for controlled local delivery to act as "radiosensitizers" and anti-inflammatory co-mediators while synergizing with the brachy-radiotherapy or other prescribed energy sources, to accelerate target cell population apoptosis with/without down regulation of procedure induced benign cellular hyperproliferation and fibrosis and/or infection.

Optionally, an embodiment of the implantable device (e.g., the layer/barrier device of FIG. 1, or the radiospike/radioanchor device (FIGS. 8, 9) or seed discussed below) contains a drug component which is controllably activated by an externally applied energy source. More specifically, a portion or element of the device includes one or more of the chemical and/or drug agents described above in connection with FIGS. 1–3. Such agents may be integrated as a polymeric or other carbon based layer or segment of the device. The agent can be pre-loaded in the device, added on after implant, or existing in either liposomal, micro-bolus packets or injectable free-form, etc. Such elements may be biologically degradable.

In this embodiment, the component containing the chemical agent is designed to controllably release the agent into the adjacent tissue upon exposure to a prescribed form, quantity and intensity of energy such as ultrasound, ionizing radiation, magnetic field, or light. Upon activation, the release of the agent can be immediate, delayed or progressive, depending on the selected the composition properties. The release can be induced by preemptive design as to the material atomic and molecular bonding and density properties which would have time and energy dependent degradation characteristics. For example, a specific milligram dosage of cortico-steroid or other anti-inflammatory or antibiotic anti-cell mitotic drug may be present in a dosed channel or pocket within the implanted dural barrier unit. As the surrounding energy degradable polymer material is gradually exposed to a prescribed activation dose units of radiation (centigray), ultrasound (total megahertz units), magnetic field induction (time exposure of gauss units), total photon light dose (time of flux units), or the like, linear gradient breakdown and release of the agents will occur with benefit to the adjacent tissue.

This externally activatible device would be packaged to indicate the dosage and name of the one or more drug or chemical agents contained therein and the prescribed activation energy type and dosage for optimal effect. Therefore, the desired clinical benefit of treatment could be achieved by the combination of therapeutic radiation/energy delivery, barrier or structural support, and activated local drug therapy directly administered to synergize with the emitted energy, both to minimize local scarring and fibrosis, as well as to accelerate local healing.

It is expected that the concomitant administration of the aforementioned therapeutic brachy radiotherapy alone or with anti-fibrotic drugs, and/or magnetic field therapy are integrated within, attached to, or adjacent to the primary element of the radioemitting device with primary intent for localized treatment to minimize postoperative fibrosis about the dura mater and neural elements of the spine following spinal surgery or procedures of any kind and associated complications and with secondary intention to potentially reduce risk of infection or poor wound healing. It should be noted that the magnetic field treatment may also be applied in order to intentionally deflect, attract or focus emitted beta particles, electrons or other charged particle radiation at controlled doses to the target soft or bone tissue and structures.

The present invention is particularly advantageous because conventional external beam radiotherapy techniques are prohibitive of pragmatic administration for the following reasons. Treatment would likely only be indicated post operatively, for those with indications for therapy, which would be difficult to perform simulation and external beam therapy set-up due to required patient positioning, tissue and dose targeting issues, location of radiotherapy facilities, patient pain control and monitoring and timely provision of the radiation dose before the optimal therapeutic window passes shortly after surgery is completed.

B. Implantable Radiospike/Radio-Anchor Embodiments

Figure 8:
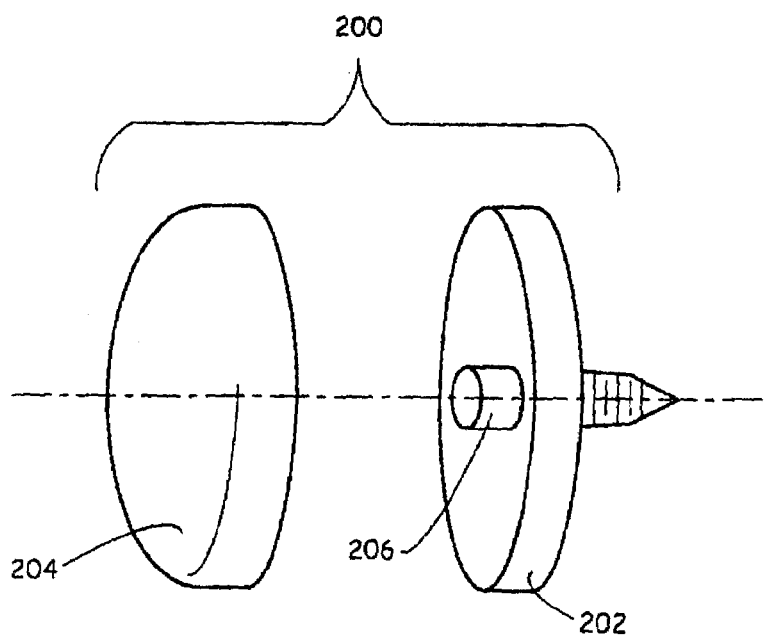
FIG. 8 is a schematic view of an implantable device constructed in accordance with teachings of the invention, the device having an anchor portion which is securable to bone.
Figure 9:
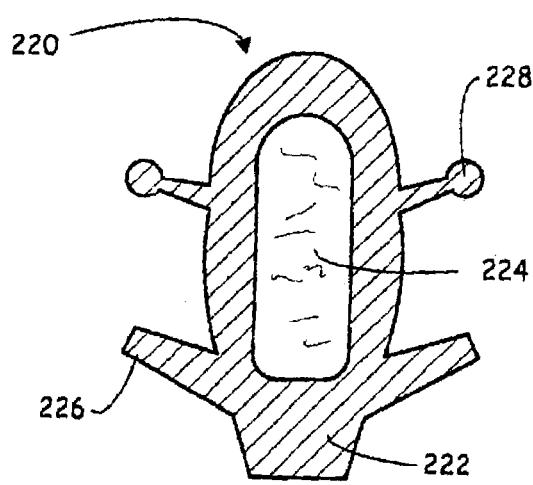
FIG. 9 is a sectional view of a further implantable device according to the present invention in an alternative configuration.

Demonstrating the variety of forms in which an implantable device according to the invention may be provided, FIGS. 8 and 9 illustrate respective radiospike or radio anchor type devices 200 and 220, respectively, each of which is securable to bone or tissue. Such devices may be implanted in tissues for spinal, paraspinal, paravertebral, paradural, or extremity related brachytherapy applications. In an efficacious application, the device 200, 220 is a mini or micro bone implantable autonomous unit, a plurality of which are permanently or temporarily affixed to specific segments of the postoperative spine or other bone/soft tissue site as placed at the time of surgery.

Referring to FIG. 8, the device 220 includes an anchor base 202 and a radionuclide-containing module 204. The anchor base 202 includes at least one anchor element 208 adapted for anchoring to bone or soft tissue. As illustrated, the anchor element 208 is shown as a threaded screw-like structure which would be appropriate, for example, for fixing to bone. Those skilled in the art will recognize, however, that anchor elements of other generally known types would also be suitable within the context of the invention. The anchor base 202 and module 204 may be provided together as an integral unit or as separate components configured for mounting together as a cooperative assembly. In the latter embodiment, the module 202 secures to the anchor base 204 with a connector structure 206 such as a snap, threads or other suitable means. This enables the anchor base 202 to be used with a variety of module types and configurations. Additionally, the anchor base 202 may be anchored to the bone or tissue prior to mounting of the module 204 thereto, for an easy and accurate implantation.

The radionuclide containing module 202 may be metallic, metallic alloy, polyethylene or other hardened plastic derivative, including graphite or titanium, or a combination of these, whereby the foundation unit is placed which contains a specific crevice, linking, or insertion component, by design, to accommodate a mono or multi-unit radionuclide containing/or loadable module. This may include elements that enable precise orientation and attachment of permanent, dissolvable, or removable catheters that are loadable radionuclides (gas, liquid, solid, gel-like) or radiopharmaceutical components. The module 202 preferably includes external markings of the type described above in connection with FIGS. 1 and 2 to aid a surgeon in selection and properly placing the module 202. Such marking is desirable to ensure assure that the physical and energy characteristics of the applied therapeutic radionuclide would provide accurate prescribed ionizing radiation or other energy deposition to the correct volume of target tissue, at the correct dose rate and correct total dose, while physically minimizing direct or scatter radiation/energy dose to unnecessary normal tissue. This may include co-integration with the chemical agents and/or magnetic field therapy as described for the energy dural barrier system. The treatment may include forms of energy emission, dose ranges, radionuclides, etc. as described above in connection with the previously described embodiments.

Another style of radiospike device 220 is illustrated in FIG. 9. The device 220 includes an exterior casing 222 constructed, for example, of titanium or another material as described above. The device includes energy containment channels for containing the radionuclide component 224. In an embodiment, the device could be configured for implantation as a free-floating "seed," although the device 220 illustrated in FIG. 9 is equipped with at anchor elements 226, 228 adapted for securing to tissue or bone.

C. Implantable Radio-Fluid Delivery Device

To facilitate delivery of energy by external sources, the invention further includes a system having an implantable fluid-delivery device which is connectable to an external fluid source. For example, FIG. 5 illustrates an implantable catheter 100 including a lumen having an inlet portion 102, an outlet portion 104, and an implantable lumen array 106 intermediately between the inlet and outlet portions 102, 104.

Figure 6:
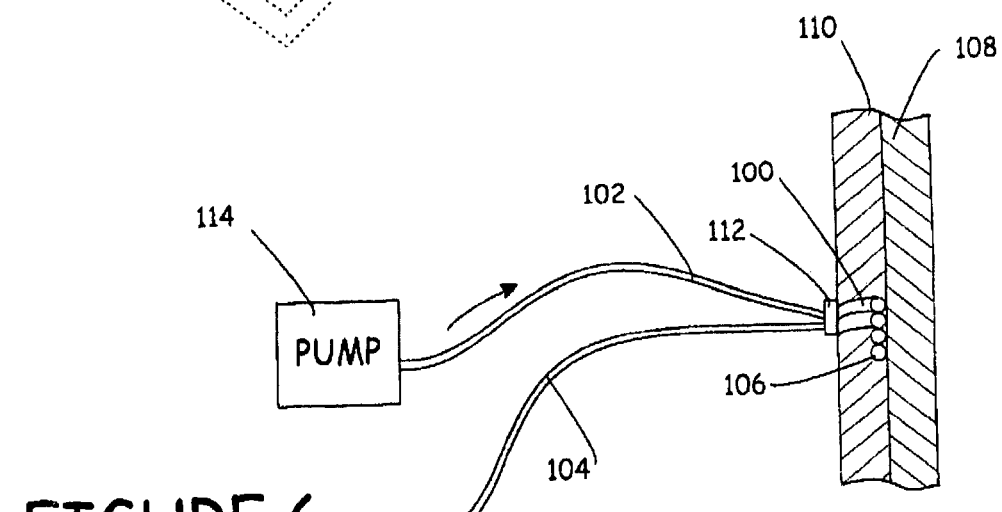
FIG. 6 is a schematic view of a fluid radionuclide delivery system including the catheter of FIG. 5 shown in an implanted state.

Referring to FIG. 6, a connector port 112 is provided at the skin surface for detachable connection of the inlet and outlet portions 102, and 104. The lumen away 106 is configured for surgical implantation adjacent a tissue 108 to be treated, under skin or other surface positioned tissues 110. In particular, the inlet portion 102 is connectable to a fluid delivery pump 114. The catheter 100 may be provided in a size and shape configuration as needed to deliver energy to a desired site. Radioactive fluid is delivered by an external pumping source, injector or reservoir/loading unit 114 into the inlet portion 102 of the lumen to circulate through the lumen away 106 and exiting through the outlet portion 104. The fluid may be in the form of a gas, liquid or gel. Preferably, the catheter 100 is constructed of a substance which degrades or dissolves in vivo after the radiotherapy dose is administered. The catheter 100 may also be extracted in vivo, in delayed fashion by an externally remaining string-like attachment, or tabs, reels, or the like, after the radiotherapy dose is administered.

Figure 5:
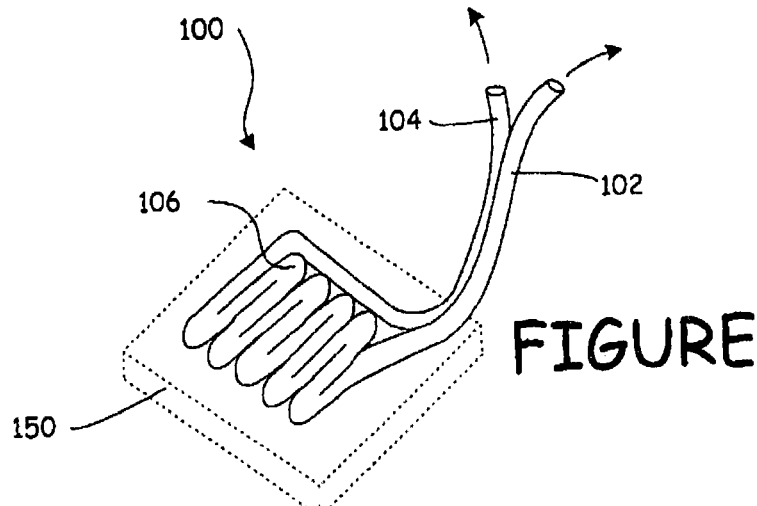
FIG. 5 is a perspective view of an implantable catheter according to an optional embodiment of the invention for delivering a fluid radionuclide.

In an embodiment, the catheter 100 further includes a layer-shaped component 150 adjacent to, or surrounding, the implantable lumen array 104, as illustrated in FIG. 5. The lumen array 104 is embedded in component 150 which may contain a radionuclide component, attenuation barrier and/or drug or chemical agent as described above in connection with the device 50 of FIGS. 1–3.

As described in connection with the embodiments above, to aid in selection and orientation, the implantable catheter 100 preferably includes visible exterior markings, such as words, lines, dots, numbers, colors, or a combination thereof, with palpable surface changes (such as bumps, rough surfaces, etc.) in order to facilitate optimal placement, orientation and alignment. The markings may further indicate the characteristics of the delivery capacity, energy delivery area of the lumen array, and/or indicate dosage information of a radionuclide-containing component, such as the layered component 150.

D. Implantable Ultrasonic Transducer Embodiment

Figure 7:
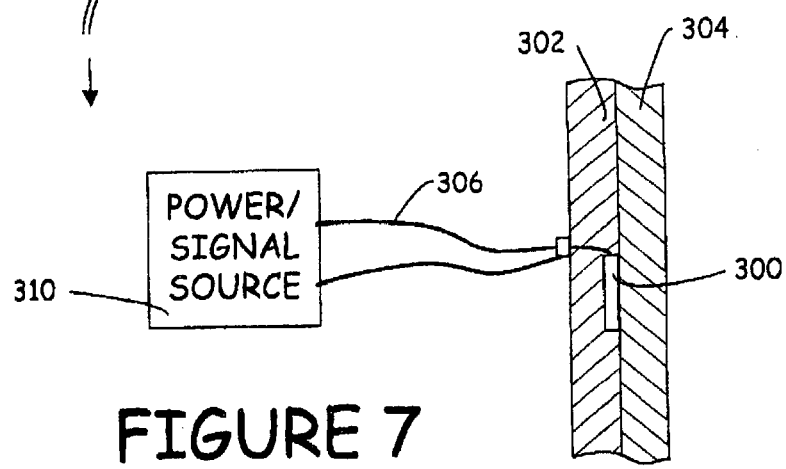
FIG. 7 is a schematic view of another optional embodiment of the invention including an implantable transducer connected to a signal-generating device for actuating desired radiant energy.

Referring now to FIG. 7, the present invention further includes a treatment system including an ultrasonic transducer unit 300 adapted for specific and identifiable implanted placement under surface tissues 302 adjacent to a tissue to be treated 304. The transducer unit 300 includes a housing compatible with the surrounding tissue and is surgically placed at a tissue site requiring treatment. The transducer 300 is activatible to administer ultrasonic wave energy during surgery and/or after the procedure is completed. In the illustrated embodiment, one or more lead 306 extends externally for connection to a power source and/or signal-generating source 310 for actuation in a prescribed manner. Of course, appropriate externally visible indicators are preferably provided on the transducer housing to assist in the proper selection of the type of transducer unit, its output frequency ranges and capacity, its proper orientation, etc, as described above in greater detail above in connection with the device of FIGS. 1 and 2. Additionally, to provide additional treatment of the surrounding tissues, the transducer unit 300 may be surrounded by or attached to one or more layers (not shown) containing a radionuclide component, attenuation barrier and/or drug or chemical agent as the element 150 described in connection with the implantable catheter of FIGS. 5 and 6.

The ultrasound emitted energies may be produced at higher than standard megahertz frequency range as used for current diagnostic clinical purposes. There is some initial clinical evidence that higher frequency and higher output ultrasound therapy may provide a clinical benefit by reducing or inhibiting hyperproliferative or excessive fibrotic and inflammatory cellular response when applied to the appropriate target tissue after localized interventional or surgical procedures.

The barriers can include complete or partial interval segments/pockets which contain a specific group of gel, liquid, or solid substances that optimize directional transmission of ultrasound wave energy to expected or prescribed depths and intended energy rates of administration. As such, the barrier would therefore by design and function be considered a novel component of integration in order to administer and transduce the ultrasound treatment, while simultaneously providing a protective barrier, and possibly concurrent or time delayed local administration of ionizing or thermal radiation and/or the chemotherapeutic/anti-inflammatory drugs as previously described.

Constructive channels, pockets, attachment units or the like may provide placement points for the ultrasonic probe and/or catheter unit, within or abutting the energy barrier element, thereby enabling conformal energy delivery to the epidural, paraspinal, or equivalent target tissue areas.

Labeling and matching components, both for the implanted barrier and the ultrasonic or irradiating unit (including any form of photon, electron, or other particle emission energy whether from an electrically generated or radionuclide source), may be denoted by written/colored symbols, palpable external surface variations (ridges, elevations, divots, etc.) designed to ensure matching positions and orientations of these therapeutic elements for optimal, reproducible efficacy.

E. Transpinal/Transdermal-Radiocatheter

Figure 10:
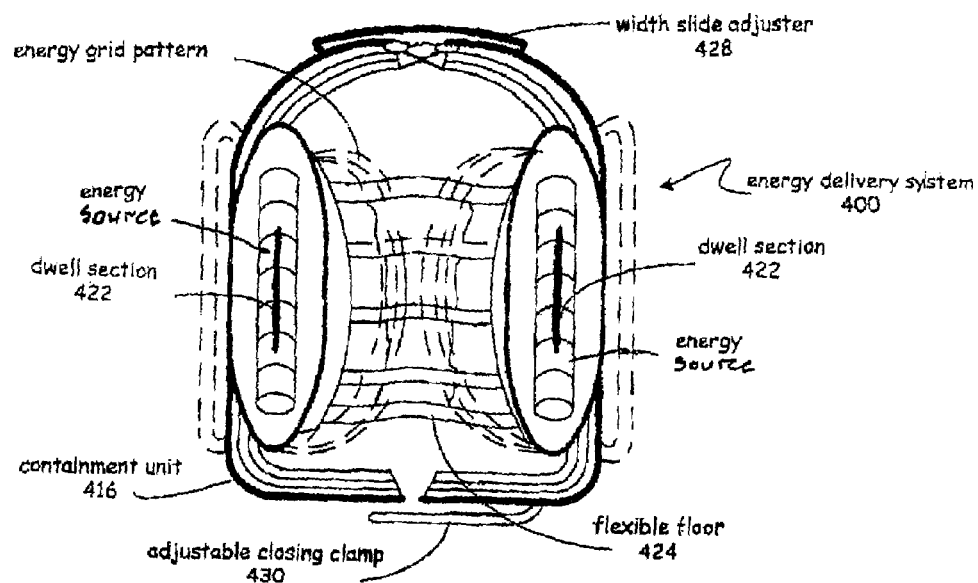
FIG. 10 is an enlarged perspective view of one preferred embodiment of the brachytherapy device of the present invention for the controlled, directional delivery of intermediate or even high dose therapeutic energy sources to spine tissue.
Figure 11:
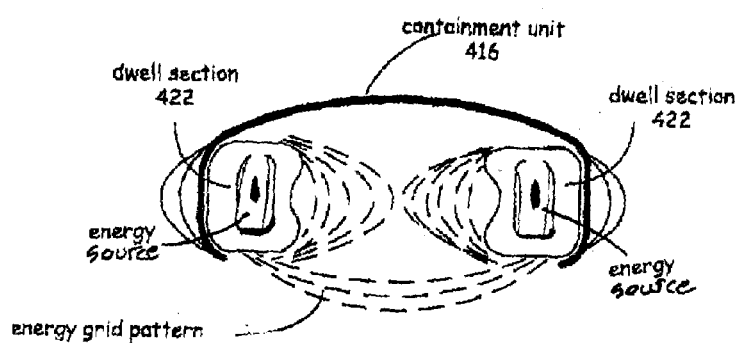
FIG. 11 is a cross-sectional view of the brachytherapy device of FIG. 10, shown from above.

FIGS. 10 and 11 depict a preferred embodiment of an alternative treatment system utilizing the teachings of the present invention. This brachytherapy energy delivery system 400 enables the controlled, directional delivery of intermediate or even high dose therapeutic energy sources intra-operatively, in real time to spine tissue.

The system 400 provides a mechanism to place a pre-designed and pre-calibrated permanently, or more likely, temporarily implanted brachytherapy component into the spinal, peri-spinal, or other like sites. The system 400 includes a pair of configured energy source dwell sections 420 abutting the outer wall and positioned opposite each other. The dwell sections 420 enable the administration for generic or customized radio or other therapeutic energy sources. The energy emission pattern are shown at 432.

A flexible "hinge" back 440 enables for the lateral bending and alignment of the system 400 within the spinal operative site. An adjustable closing clasp 430 stabilizes the shape and positioning of the system 400 after initial placement and hinge closure, and enables optimization for space and treatment margin. The system 400 is specifically designed to avoid pre-implant "energy barrier" shaping and cutting, by adjusting the "hinges" "width slide adjuster" or the "adjustable closing clamps 430."

The system 400 also includes a depressed flexible floor 424 to accommodate variable paraspinal tissue depths and to control the degree and the quantity of energy penetration. The flexible floor 424 provides for energy shape, direction, and penetration control in order to create a targeted, directional "energy grid." This grid enables optimization of the intended coverage dose to the immediate targeted tissue and margin(s) within the operative site, while minimizing excessive deep or lateral doses to adjacent nerve or other soft tissue. The flexible floor 424 overlays the operative spine site at the base of defect upon the dura, peri-dural, or scar-risk tissue. The flexible floor 424 enables better handling and dosimetry profiling for temporary high dose rate treatments.

The metal alloy combinations of choice as in the previous embodiments include, polycarbon compound constituents, energy activated dissolvable components, magnetized segments, and radionuclide-source options all apply. This also includes wall designs with energy attenuation intended components, as well as, palpable and visible orientation markers, radio-opaque markers (for x-ray visible position verification), and loadable energy source physical constructs (seeds, wires, liquids, gasses, gels, plaques, or custom carrier designs). Additionally, the "flexible" components of this design have a nitinol or equivalent alloy integration to exploit their "metal-memory" structure properties. As best seen in FIG. 11, the energy-emitting barrier is preferably "horse-shoe" shaped.

Chronic back pain is also recognized as a major health debilitation for which a specific surgical procedure may not be indicated to achieve identifiable benefits. The origin of such pain related dysmobility is not routinely attributable to an objective causative factor from one person to another. Within the spine related medical literature, the chronic pain syndrome has been clinically correlated to probable pathology origins within or about the intervertebral discs of the spine. Clinical theories and related practice within the surgical and non-surgical spine specialties have described and defined single and/or combined local origins of such variable non-malignant, non-surgical, pain as related to nocioreceptors, excessive edema, hyper-inflammatory cellular response with some necrosis or chronic exacerbation of all of these elements due to prior injury and/or unstable physical stress effects upon the disc and associated tissues.

Current or prior treatments approaches have included various external heat/massage manipulations or systemic and local drug therapies including non-steroidal or corticosteroid agents. Other tried direct options include interventional percutaneous or open administration of a catheter wire based electro-stimulation, hyperthermia (heat), cryotherapy (cold), or possible laser energy source ablation of the vertebral discs or related tissue. All have been applied or investigated with varying degrees of relevant clinical success and/or longevity and predictability of efficacy.

Chronic or acute pain of the spine, symptoms of spinal cord compression, and other corporal sites of bone or soft tissue pain related to hyper-inflammatory or hyper-stimulation of nocioreceptors have been established as effectively manager/treated with palliative doses of ionizing radiation therapy when such symptoms originate from oncologic disease. Such prescribed doses related to "palliative" range therapy has also demonstrated a most acceptable toxicity profile with regards to minimal risk of short and/or long term side effects whether to nerve tissue, bone or functional soft tissue. This has been demonstrated either with conventional or modern techniques of administering therapeutic radiation with either external beam or brachytherapy methodologies. Furthermore, as discussed in previous sections, multiple benign disease processes, whether due to hyper-inflammatory states, excessive hyperproliferative tissue growth, and/or local benign tumor growth have all been successfully treated with low to moderate doses of ionizing radiotherapy with excellent normal tissue tolerance when proper technique is utilized by trained physicians.

The previously described embodiments, references, and background have provided rationale as to possible concomitant or sequential therapy modalities. Such principles are based upon known proven or scientifically inferred effects of controlled energy doses and properties of multiple energy sources and their unilateral, combined, or synergistic effects upon each other. More specifically, such energy sources are fundamentally based upon ionizing radiation sources (whether originating from a radionuclide source suitable for medical treatment or electrically generated) producing photons, electrons, particle energy, etc. Secondary energy source priority for such methods and/or devices would focus upon high frequency/high energy ultrasound (crystal based with electrical or magnetic generation) at or above conventional diagnostic ranges. These two optional perfunctory energy sources may be incorporated in conjunction with such shared device use with local area magnetic field induction, hyperthermia, or electrocautery type energy sources. Again, with the requirement that ionizing radiation and/or high frequency ultrasound energy are the primary therapeutic energy source for direct cellular effects, while the other energy sources are intended as adjunctive, i.e., to enhance or to further control dose or direction of radiation or ultrasound, or to protect adjacent normal tissues from adverse effects.

To induce a magnetic field, for example, a magnetic-property containing element is directly or separately attached or integrated or impregnated upon the internal or external surfaces of an appropriate device. The magnetic field inducing material may be made of any known, biologically safe heavy metal, metal alloy, or electrically induced magnetic material (causing field shift of atomic shell electrons) in order to "directionally shift" electron or beta particle radiation toward the targeted tissue or to repel similar charged particle energy away from tissue. The treatment may optionally or alternatively include the application of heat, as discussed herein.

Alternative design options would provide for collaborative localized administration, adjunctively, of certain anti-inflammatory, cortico-steroid type, anti-mitotic, and/or anti-infective chemical agents, not as primary treatments for the intended clinical benefit, but as supportive agents that are requisite to the fundamental energy dose and thereby involved or activated in desired dose preparation via the device and methods required to administer the energy sources by trans-spinal interventional techniques.

In the medical field of radiation oncology, there is a significant body of clinical science which provides a sound foundation for the rationale of improved control of onco-cellular treatment response for resilient cells, with the sequential combination of external beam radiotherapy followed by interstitial hyperthermia at controlled temperature and time. Such tissue response is not as efficacious or safe with hyperthermia alone nor has it been demonstrated to work with adjunctive magnetic field or ultrasonic therapy. For example, any of layers 50A–50D, or an additional layer, can be a layer having magnetic field properties. Therefore, the potential benefit exists that localized, controlled dose brachytherapy radiation to the target tissue within or about the disc will have improved outcome when followed by short duration hyperthermia given through the same catheter, implant-module apparatus and/or pseudo needle cannulae in order to inhibit or minimize hypercellular/hyperinflammatory activity and/or desensitize pain nerve receptors or edema causing back pain and repetitive back instability.

Desired dose ranges of radiation to the paravertebral tissue will be 400 cGy to 5000 cGy total dose at dose rates of 1–100 cGy/hr or 10–500 cGy/minute prescribed to predictable planned tissue target volume accuracy ranges of 1 mm to 50 mm, depending on the radiation emission type and/or whether a radionuclide/radiopharmaceutical or electromagnetic source is applied. Desired heat energy deposition, again whose use is requisite upon the concomitant or antecedent use of radiation, high-energy ultrasound, and/or magnetic field flux, includes temperature ranges of 360 Celsius to 480 Celsius for time periods of 1–180 minutes for margin ranges of 1–100 mm. Additional but important characteristics of the delivery apparatus would include 3-D structure, morphologic materials construct etc. all intended to enable homogeneous energy distribution of ionizing radiation, radiant/convection heat, high energy/high frequency ultrasound waves or fluctuant or static magnetic fields. Such interventional therapeutic apparatus can have integrated open-end ports, pockets, channels, pods, or the like for adaptive ability to secondarily administer above described chemical and/or drug agents simultaneously or sequentially to soft tissue or bone sites being treated with the above discussed energy sources, adjunctively, to maximize desired tissue responses.

Appropriate energy sources may include, for example, appropriate humanly compatible radionuclide sources discussed above in connection with other treatment systems of the invention, including, but not limited to, any and therapeutically effective solid, liquid, gas, gel, or other intermediate phase radio nuclide or radioisotope compounds which emit gamma rays, x-rays, beta particles, alpha particles, positrons, auger electrons, photons, or any combination thereof produced by nuclear decay, isomeric transition, electron capture, fluorescent, phosphorescent or luminescent induction, external bombardment activation, electrical stimulation or any combination thereof. Specific primary radionuclides, either in stable or radioactive form include but are not limited to xenon, krypton, neon, argon, radon, technetium, rhenium, yttrium, phosphorus, iodine, strontium, samarium, gold, copper, palladium, iridium, tin, rubidium, osmium, platinum, ytterbium, cesium, americium, radium, thallium, chromium, vanadium, barium, titanium, bismuth, and rhodium. More particularly, the specific primary radionuclides of choice are yttrium, strontium, iridium, iodine, palladium, and cesium.

The aforementioned technology provides the clinical framework and scientific basis for more detailed elucidation of variable dependent and independent methods and devices to enable a trained physician/clinician to provide a minimally invasive, outpatient treatment option to improve chronic or recurrent pain or probable discogenic etiology while avoiding standard open surgical methods. In one treatment approach, the suspected abnormal or pain inducing disc levels of the human spine are identified by an appropriate clinician using accepted clinical history and exam, imaging/radiographic, and/or electromyographic criteria for diagnosis and localization of discogenic pain, whether due to prior trauma, partial herniation, excessive fibrosis, hyperinflammation, or hypersensitivity of pain receptors. Thereafter, local anesthesia and/or limited general anesthesia may be given to the skin and/or sub-cutaneous tissue so that the most direct perpendicular or angulated approach from the skin surface of the back/neck to the targeted disc levels, allowing the shortest, safest distance for an introducer needle or catheter (after a small incisional cutdown) to reach the desired soft tissue/paravertebral target area.

Specifically, an "introducer" type catheter, needle or pseudoneedle (coring or non-coring), or port system would have a desired internal diameter ranging from 36 gauge to 6 gauge and/or "French" size of 1 to 34 in diameter. In various embodiments, these transcutaneous/transpinal variable internal diameter cylindrical like units may be of different lengths, may be flexible, partially malleable, capable of rotational orientation under direct visual or radiographic imaging, or fixed with limited or no bendability either entirely or as sections such as the proximal, middle or distal segments. In such a catheter, a single or whole column preferably contains >0 to 100 cc volume or 0.5 to 500 mCi/cc or 1–1000 mCi total activity.

More than one cylindrical, triangular, rectangular, or other polygonal tube (as described above) can be integrated, in linear unison or as parallel units about or in-line with each other and either directly abutting each other or separated but with attachable components for stability. They can be conducive for passing stiff or flexible guide wires for recannulation or threadable guidance. In order to provide intra-disc maneuverability, the distal ends can be torqueable. Additionally, the units may be provided with various end configurations being open, closed or having side ports. Optionally, a fenestration port can be provided along the shaft length or ends to allow for administration of liquid, gas, or gel-like chemical/drug agents which may be inert or non-inert substances with carrier compounds and/or radiopharmaceuticals. The guiding/localizing tubes, needles, introducers, etc. may be composed of various materials, including composites, plastics, metal alloys, natural or synthetic rubbers, metals, metal-alloys, bio-compatible molecular chain compounds, viton rubber, polyurethane, polyethylene, polyimide, polyvinylchloride, polyamide, polytetra fluoroethylene, and silicone. Specific segments or entire linear tracings can have combinations of radiopaque metal alloy elements that allow radiological, internal localization and three-dimensional orientation.

Attachable or fixed "treatment" specific units, typically at the terminal segment of the unit can be designed to coil, bend-back upon itself, fold in perforated angles, or remain straight and detachable within or about the targeted disc/paravertebral tissue which can be pre-filled, loaded during the procedure, or loaded after placement with a specific radionuclide source (discussed above) or conductance metal element able simultaneously transfer electrical generated ionizing radiation or electrical impulse. The treatment segment can be sealed, sealable or with closed-delayed injection access for adequate non-leak containment of a radiofluid (gas, liquid, or gel either inert or not) with the surrounding material allowing transmission of specific prescribed radioemissions to provide homogenous doses of radiation to the target tissue. The material can contain all or portions which when exposed to an expected dose range of energy, heat, ultrasound, etc., undergo accelerated biodegradability and dissolution to that section, dependent upon the physical half life of the radionuclide. Another option can include that the treatment unit remains attached to the transdermat tube, wire, needle, or catheter element in order to allow delayed injection loading or high dose rate or low dose rate after loader based brachytherapy, for one or more treatments, with subsequent detachment of the introducer elements from the treatment unit. Include mini-volume balloons, pockets, channels etc.

As described the same or parallel traversing "tube" units can provide for injection of chemical elements to the same target tissue. They can also have a radio fluid tight proximal, externally dwelling, port unit. Other lumen segments can provide for a flexible, guidable wire which is conducive and placeable to the level of the radio-treatment unit for heating (hyperthermia) and/or with an end point crystal-like transducer capable of high frequency ultrasound, to be administered before, during, or after the planned radiation dose.

The transpinal and transcutaneous and external residual length of the device can have specific metal alloy and/or plastic coatings or integrated element to the lumen wall thickness to act as safety radioattenuating shielding, heat protection shielding, or other electromagnetic emissions beyond the target tissue region, depending if primary photons or Beta or other particle energies are emitted.

Pre-fixed magnets and/or electro-magnetic conducting solenoid wire or metal materials can be placed on one or more of the placed tubes or upon/within the "treatment" unit to intentionally accelerate and/or directionally control charged particle energy, or to expose the energy treated tissue to specific time and gauss units of magnetic field to accentuate efficacy or enhance normal tissue tolerance or healing. Another embodiment includes placement of an intraluminal, magnetized flexible wire like element via the "tubes" to the targeted disc tissue.

The catheter devices according to the present invention preferably include direct or attachable labeling of the type described above in connection with other embodiments of the invention to assist in proper selection, use, and positioning of the catheters, heat units, magnetic field units, ultrasound energy units devices for a desired treatment affect.

Throughout this application, various U.S. patents, and applications are referenced by number and inventor. The disclosures of these Patents and Applications in their entireties are hereby incorporated by reference into this specification in order to more fully describe the state of the art to which this technology pertains.

It is evident that many alternatives, modifications, and variations of the brachytherapy device and method of the present invention will be apparent to those skilled in the art in light of the disclosure herein. it is intended that the metes and bounds of the present invention be determined by the appended claims rather than by the language of the above specification, and that all such alternatives, modifications, and variations which form a conjointly cooperative equivalent are intended to be included within the spirit and scope of these claims.

We claim:

1. An implant device for delivering a predetermined dosage of energy treatment to reduce chronic back pain or scarring or inflammation, the implant device comprising: a. an energy emitting material disposed relative to the implant device to provide the therapeutic energy treatment to tissue proximate to the spinal cord after a surgical procedure; b. an energy-producing layer, the energy-producing layer being capable of pre-implantation shaping, the energy-producing layer being adaptable for surgical placement at a surgical site, the energy-producing layer providing desired treatment effects to the tissue proximate to the spinal cord; c. a layer having magnetic field properties, the magnetic field layer directionally shifting particle radiation toward the targeted tissue proximate to the spinal cord or repelling similar charged particle energy away from the targeted tissue proximate to the spinal cord; and d. attenuating barrier components to facilitate a precise directional focusing of therapeutic energy to the targeted tissue while shielding adjacent non-targeted tissue from unnecessary exposure; wherein the implant device is placed proximate to the spinal cord during the surgical procedure, the implant device being integrated into a position relative to the spinal cord to provide a beneficial three dimensional delivery of the therapeutic energy treatment to the tissue proximate to the spinal cord.

2. An implant device for delivering a predetermined dosage of energy treatment to reduce chronic back pain or scarring or inflammation, the implant device comprising: a. an energy emitting material disposed relative to the implant device to provide the therapeutic energy treatment to tissue proximate to a spinal cord after a surgical procedure; b. a barrier that is capable of pre-implantation shaping, the barrier being adaptable for surgical placement at a surgical site, the barrier providing desired treatment effects to the tissue proximate to the spinal cord; c. a layer having magnetic field properties, the magnetic field layer directionally shifting particle radiation toward the targeted tissue proximate to the spinal cord or repelling similar charged particle energy away from the targeted tissue proximate to the spinal cord; and d. attenuating barrier components to facilitate a precise directional focusing of therapeutic energy to the targeted tissue while shielding adjacent non-targeted tissue from unnecessary exposure; wherein the implant device is placed proximate to the spinal cord during the surgical procedure, the implant device being integrated into a position relative to the spinal cord to provide a beneficial three dimensional delivery of the therapeutic energy treatment to the tissue proximate to the spinal cord.

\* \* \* \* \*